(12) United States Patent
Gollasch et al.

(10) Patent No.: US 8,219,198 B2
(45) Date of Patent: *Jul. 10, 2012

(54) METHOD AND DEVICE FOR USING IMPEDANCE MEASUREMENTS BASED ON ELECTRICAL ENERGY OF THE HEART

(75) Inventors: Maik Gollasch, Berlin (DE); Eckhard Alt, Houston, TX (US)

(73) Assignee: Medtronic, Inc., Minneapolis, MN (US)

( * ) Notice: Subject to any disclaimer, the term of this patent is extended or adjusted under 35 U.S.C. 154(b) by 8 days.

This patent is subject to a terminal disclaimer.

(21) Appl. No.: 12/857,140

(22) Filed: Aug. 16, 2010

(65) Prior Publication Data

US 2011/0087119 A1    Apr. 14, 2011

Related U.S. Application Data

(63) Continuation of application No. 11/104,389, filed on Apr. 11, 2005, now Pat. No. 7,778,709, which is a continuation-in-part of application No. 10/622,184, filed on Jul. 16, 2003, which is a continuation-in-part of application No. 10/155,771, filed on May 25, 2002, now Pat. No. 6,829,503.

(30) Foreign Application Priority Data

Oct. 1, 2001    (DE) .................................. 101 48 440

(51) Int. Cl.
*A61N 1/378*    (2006.01)
(52) U.S. Cl. ............................................. 607/35; 607/9
(58) Field of Classification Search ................. 607/9, 17, 607/34, 35
See application file for complete search history.

(56) References Cited

U.S. PATENT DOCUMENTS

| | | | |
|---|---|---|---|
| 3,693,625 A | 9/1972 | Auphan | |
| 3,842,843 A | 10/1974 | Mourot et al. | |
| 3,906,960 A | 9/1975 | Lehr | |
| 4,690,143 A | 9/1987 | Schroeppel | |
| 4,884,576 A | 12/1989 | Alt | |
| 4,899,758 A | 2/1990 | Finklestein et al. | |
| 4,905,705 A * | 3/1990 | Kizakevich et al. | 600/509 |
| 4,919,136 A | 4/1990 | Alt | |
| 5,003,976 A | 4/1991 | Alt | |
| 5,024,222 A | 6/1991 | Thacker | |
| 5,309,917 A * | 5/1994 | Wang et al. | 600/508 |
| 5,331,966 A | 7/1994 | Bennett et al. | |
| 5,342,408 A | 8/1994 | deCoriolis et al. | |
| 5,643,328 A | 7/1997 | Cooke et al. | |

(Continued)

FOREIGN PATENT DOCUMENTS

WO    WO 2004/032788 A2    4/2004

(Continued)

OTHER PUBLICATIONS

Fricke et al., *The Electric Conductivity of and Capacity of Dispersed Systems*; Physics 1931; 1:106-115.

(Continued)

*Primary Examiner* — Brian T Gedeon
(74) *Attorney, Agent, or Firm* — IPLM Group, P.A.

(57) ABSTRACT

A method and a device are disclosed for evaluating the cardio-circulatory and pulmonary condition of a patient, including determining the patient's thoracic impedance based on information solely derived from the electrical energy generated by the patient's own heart.

23 Claims, 12 Drawing Sheets

U.S. PATENT DOCUMENTS

| | | | |
|---|---|---|---|
| 5,782,884 | A | 7/1998 | Stotts et al. |
| 5,792,197 | A | 8/1998 | Nappholtz |
| 5,792,205 | A | 8/1998 | Alt et al. |
| 5,876,353 | A | 3/1999 | Riff |
| 5,879,308 | A * | 3/1999 | Rasanen .................. 600/536 |
| 5,899,928 | A | 5/1999 | Sholder et al. |
| 5,920,310 | A | 7/1999 | Faggin et al. |
| 5,957,861 | A | 9/1999 | Combs et al. |
| 5,987,352 | A | 11/1999 | Klein et al. |
| 6,080,187 | A | 6/2000 | Alt et al. |
| 6,104,949 | A | 8/2000 | Pitts-Crick |
| 6,190,324 | B1 | 2/2001 | Kieval et al. |
| 6,336,903 | B1 | 1/2002 | Bardy |
| 6,351,667 | B1 | 2/2002 | Godie |
| 6,381,493 | B1 * | 4/2002 | Stadler et al. .................. 607/9 |
| 6,416,471 | B1 | 7/2002 | Kumar et al. |
| 6,445,956 | B1 | 9/2002 | Laird et al. |
| 6,456,256 | B1 | 9/2002 | Amundson et al. |
| 6,470,212 | B1 | 10/2002 | Weijand et al. |
| 6,473,640 | B1 | 10/2002 | Erlebacher |
| 6,497,655 | B1 | 12/2002 | Linberg et al. |
| 6,512,949 | B1 | 1/2003 | Combs et al. |
| 6,512,953 | B2 | 1/2003 | Florio et al. |
| 6,600,949 | B1 | 7/2003 | Turcott |
| 6,640,137 | B2 | 10/2003 | MacDonald |
| 6,721,597 | B1 | 4/2004 | Bardy et al. |
| 6,813,514 | B1 * | 11/2004 | Kroll et al. .................. 600/509 |
| 6,829,503 | B2 | 12/2004 | Alt |
| 7,778,709 | B2 * | 8/2010 | Gollasch et al. .................. 607/35 |
| 2002/0013613 | A1 | 1/2002 | Haller et al. |
| 2002/0055761 | A1 | 5/2002 | Mann et al. |
| 2002/0115939 | A1 | 8/2002 | Mulligan et al. |
| 2003/0074029 | A1 | 4/2003 | Deno et al. |
| 2003/0114898 | A1 | 6/2003 | Von Arx et al. |
| 2003/0139783 | A1 | 7/2003 | Kilgore et al. |
| 2007/0078492 | A1 | 4/2007 | Tozzi et al. |

FOREIGN PATENT DOCUMENTS

WO    WO 2007/109272 A2    9/2007

OTHER PUBLICATIONS

Geddes L. et al., *The Specific Resistance of Biological Material: A Compendium of Data for the Biomedical Engineer and Physiologist*, Medical and Biological Engineering 1967, 5:271-293.

Geddes et al., Medical and Biological Engineering 1967, 11:336-339.

Carter et al., Chest 2004, 125:1431-1 440.

E. Alt et al. for capture detection in connection with cardiac pacing (Pace 1992, 15: 1873-1 879.

Studies published at the 2005 meeting of the American College of Cardiology in Orlando, Florida, USA (CARE-HF study).

Louis, et al., "A systematic review of telemonitoring for the management of heart failure," The European Journal of Heart Failure 5 (2003) 583-590.

Valina et al., "Subcutaneous Impedance Monitoring for Detection of Low Cardiac Output and Fluid Overload," American Heart Association Scientific Sessions 2003, abstract tracking No. 03-SS-A-17350-AHA.

Langreth, "The Doctor Is In: predicting and treating disease will get a whole lot easier when monitors are implanted," Forbes Magazine article dated Sep. 15, 2003.

47 C.F.R. § 95.628.

\* cited by examiner

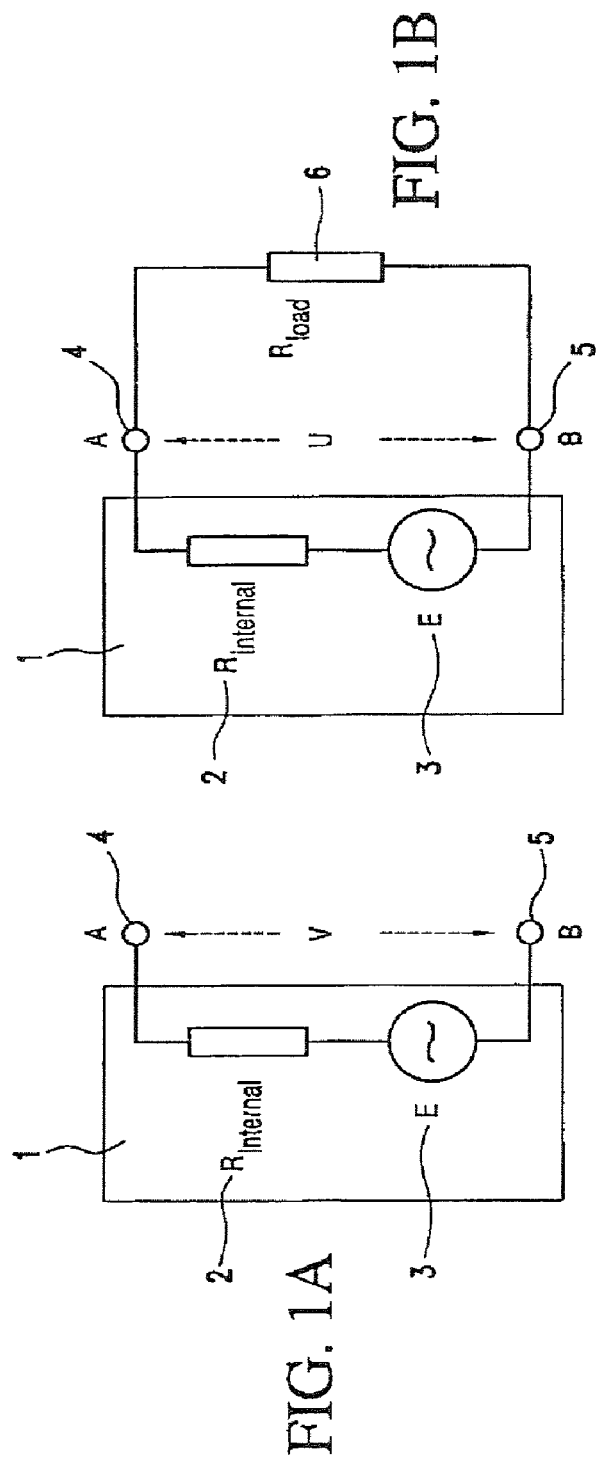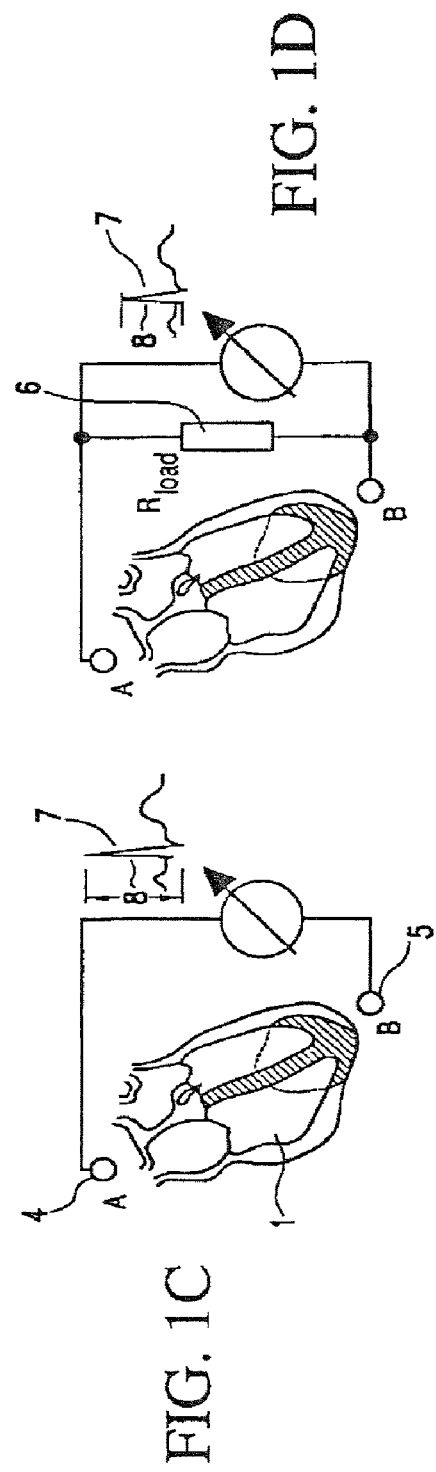

$R_{insp} \neq R_{exp} \longrightarrow U_1 \neq U_2 \longrightarrow U_1 - U_2 = \Delta U_2$ $\Delta$ = respiration

METHOD AND DEVICE FOR USING IMPEDANCE MEASUREMENTS BASED ON ELECTRICAL ENERGY OF THE HEART

RELATED APPLICATIONS

This application is a continuation of and claims priority from U.S. patent application Ser. No. 11/104,389, now U.S. Pat. No. 7,778,709, filed Apr. 11, 2005, which is a continuation-in-part of U.S. patent application Ser. No. 10/622,184, filed Jul. 16, 2003, and which is a continuation-in-part of U.S. patent application Ser. No. 10/155,771, filed May 25, 2002, now U.S. Pat. No. 6,829,503, that claims priority of DE 10148440-2, filed Oct. 1, 2001.

BACKGROUND

The present invention relates generally to obtaining a measure of a patient's thoracic impedance, and more particularly to doing so using information derived from an EKG signal with a device that relies on electrical energy provided by the patient's own heart.

Specific resistance of biological materials and impedance measurements have played a major role in modern medicine. The electrical conductivity and capacity of disperse systems have been described as early as 1931 (Fricke et al., *The Electric Conductivity of and Capacity of Dispersed Systems*; Physics 1931; 1:106-115). Later, especially in the 1950s and 1960s, significant interest was directed towards the resistance of biological materials (e.g., Geddes L. et al., *The Specific Resistance of Biological Material: A Compendium of Data for the Biomedical Engineer and Physiologist*, Medical and Biological Engineering 1967, 5:271-293). The application of impedance and resistance measurements for cardio-circulatory function by measuring the blood and body temperature has been studied extensively by Geddes et al., Medical and Biological Engineering 1967, 11:336-339). Also, internal and external whole body impedance measurements have been used for noninvasive monitoring and determination of cardiac output (Carter et al., Chest 2004, 125:1431-1 440). In addition, the feasibility of using intracardiac impedance measurements has been evaluated by E. Alt et al. for capture detection in connection with cardiac pacing (Pace 1992, 15: 1873-1 879).

Background patents that describe the use of impedance in conjunction with implantable devices are referenced in U.S. Pat. No. 5,003,976 to Alt, which describes the cardiac and pulmonary physiological analysis via intracardiac measurements with a single sensor. The '976 patent discloses that a single functional parameter, namely intracardiac impedance, varies both with the intrathoracic pressure fluctuations following respirations and with cardiac contraction. This value is representative of both pulmonary activity and cardiac activity. The finding indicates that this information derived from intracardiac impedance can be used not only to monitor the patient's cardiac and pulmonary activity, condition and cardio-circulatory status, but also, to control the variability of the rate of an implantable cardiac pacemaker.

U.S. Pat. No. 4,884,576 to Alt et al. discloses a self-adjusting rate responsive cardiac pacemaker and method based on the intracardiac signal derived from impedance measurements using an electrode implanted into the heart. And U.S. Pat. No. 4,919,136, also to Alt, describes a ventilation controlled pacemaker which uses the ventilation signal derived from those impedance measurements with an electrode in the heart to adjust the pacing rate.

Recently, considerable interest has been focused on the monitoring of congestive heart failure by means of impedance. U.S. Pat. No. 6,473,640 to Erlebacher describes a system that detects changes in resistance to a flow of current in the systemic venous system, and detects changes in impedance to a flow of current through lungs. The specific signal processing enables a determination of congestion in the venous or in the pulmonary system by application of differential signal processing of impedance. Other methods, such as are described by Combs in U.S. Pat. No. 5,957,861 and Riff in U.S. Pat. No. 5,876,353, respectively pertain to impedance monitoring for discerning edema through evaluation of respiratory rate, and use of implantable medical devices for measuring time varying physiological conditions, especially edema, and for responding thereto.

U.S. Pat. No. 6,104,949 to Pitts-Crick relates to a device and a method used for the diagnosis and treatment of congestive heart failure. Godie, in U.S. Pat. No. 6,351,667, describes an apparatus for detecting pericardial effusion, in which a wire probe anchored to the right heart ventricle and two other wire probes are used to measure the impedance between the different probes in order to assess the degree of pericardial effusion.

U.S. Pat. No. 4,899,758 to Finklestein et al. describes a method and apparatus for monitoring and diagnosing hypertension and congestive heart failure. U.S. Pat. No. 6,336,903 to Brody relates to an automatic system and method for diagnosing and monitoring congestive heart failure and the outcomes thereof. US patent publication 2002/0115939 to Moligan et al. describes an implantable medical device for monitoring congestive heart failure in which incremental changes in parameter data over time provide insight to the patient's heart failure state.

The measurement of heart failure becomes of greater clinical interest and importance as more than 5 million patients in the U.S. are affected. With deterioration of myocardial function, patients often require repeated hospitalization. Current methods of monitoring congestive heart failure cannot reliably predict an early occurrence of this congestive heart failure; but an understanding of its occurrence may provide an early indicator of this adverse event for the patient.

A considerable number of new treatment forms have been introduced into clinical practice. It had been shown that congestive heart failure can be treated, not only by drugs, especially Beta blockers, but also by biventricular pacing. This method makes use of the exact timing of a stimulus, not only to the right ventricle or to the septum, but also to the left side of the heart by means of an electrode which is implanted into the coronary venous circulation. By these means, the left ventricle can be stimulated at a time that provides an optimal synchronization of the heart and improves the mechanical effectiveness of the systole by synchronizing the depolarization of the right heart, the septum and the left heart. This avoids the ineffective late contraction of the left ventricle at a time when the septum depolarization has already occurred, and the squeezing of the blood by synchronous action of the septum and left ventricle is no longer present. In addition, the reduction in mitral valve regurgitation by this type of resynchronization has been shown.

Studies published at the 2005 meeting of the American College of Cardiology in Orlando, Fla., USA (CARE-HF study) illustrate that not only the quality of life of those patients with New York Heart Association, Heart Failure Class 3 and 4 can be improved, but also the life expectancy. This recent data show very impressively that over a 3-year period such biventricular stimulation and the mortality can be reduced by half in a highly significant manner. An these new devices improve the survival and quality of life of patients and have a beneficial effect on re-hospitalization. Nevertheless, the occurrence of heart failure is still a major problem for these patients, and it is beneficial to detect such a heart failure as early as practicable.

A second parameter which plays a major role in patients with implantable devices such as pacemakers and defibrillators is the correct adjustment of heart rate. Rate adaptive pacemakers in the past have provided an open type of correlation between a signal parameter to adjust the heart rate and the affected heart rate. However, even multiple sensor parameters that have been used for adjustment of the pacing rate have not brought the real need of a patient to clinical practice, mainly a closed-loop monitoring of heart rate.

In the healthy person, the heart rate is regulated by a very sophisticated closed loop and negative feedback. Heart rate only increases to a level with exercise which is physiologically beneficial. This means that if a patient exercises only mildly, his heart rate increases proportional to the increase in oxygen uptake for this person which is a fraction of his maximum exercise capacity, maximum oxygen uptake and aerobic and anaerobic capacity. Thus, if someone is well-trained; an external load of 50 watts might represent only 25% of his/her maximum exercise capacity if the patient is capable of exercising up to a level of 200 watts. With this external load of 50 watt the heart rate will increase by only the fraction that is represented by the patient's resting heart rate and maximum exercise heart rate. In other words, such a well-trained person will increase his/her heart rate only by 30-35 beats per minute (bpm). A less capable patient, who has a maximum exercise capacity of 100 watts, will increase his/her heart rate with the same external load to a higher degree. In that case, the slope of increase in heart rate depends not only on a fixed relation of a sensor parameter, such as ventilation or physical activity or any other physiologic parameter having a suitable correlation with heart rate, but also on his/her underlying cardio-pulmonary exercise capacity and condition.

It is therefore a principal aim of the present invention to provide a novel method to detect a parameter that can control not only the heart rate in a physiologic appropriate manner, and provide a closed-loop feedback control for the optimal heart rate of an exercising patient, but also to monitor the individual status of the patient under a wide range of physiologic conditions including normal resting status, congestive heart failure and exercise states.

Many attempts have been made in the past to use impedance measurements to derive appropriate signals; however, the past approaches have involved use of external power sources to power the device(s) that would monitor and detect impedance. This external energy can be applied either outside the thorax from a supply external to the body, or by an implantable device that uses energy from an electrical battery housed within the device itself.

SUMMARY

It is the aim of the present invention to provide means and methods to monitor impedance of a patient by using the patient's own heart as the power source.

It is a further aim of the invention to provide a method of detecting the thoracic impedance of a person without need for a battery or other external power source or need for the respective circuitry to provide the current or voltage for the impedance measurement that has heretofore limited the availability of energy to power implantable devices, and accordingly required periodic and even relatively frequent replacement of the implanted device.

It has been long known that the EKG, which can be derived from the surface of the patient, represents a voltage generated by the heart. This voltage is derived from the skin of a patient by means of electrodes which are attached. The resulting voltage in an EKG can be detected from different leads. There are bipolar electrodes which derive a voltage, between for example Lead I the right arm and the left arm, in the way that the resulting voltage change between these two electrodes represents the main vector of the heart in projection to those leads. Therefore, the amplitude is a measurement of the voltage generated by the heart and the vector. The input impedance of an external EKG machine is standard in a range between 1-10 megohms. This means that the input impedance and resistance of such an amplifier is very high and therefore no current is shunting through the machine and the voltage always represents the maximum voltage generated from the energy source, mainly the heart. Differences in voltages with the current EKG measurement result from different vectors that project two different leads on the surface of a patient.

The same holds true for voltages detected with implantable devices from leads which are situated within the heart or within the thorax or even implantable devices which have EKG electrodes outside the thorax, such as EKG loop recorders or devices which are suitable for monitoring the EKG and congestive heart failure from electrodes that are situated outside the thoracic cage such as described by Alt et al in the aforementioned related '771 patent application.

The underlying principle of the invention may be summarized, for exemplary purposes, from experiments conducted by the applicants. The measurements that resulted from placement of standard EKG I, II, and III leads on the patient were recorded in the presence and absence of an external load. The amplitude of the EKG signal that corresponds to the measured voltage is a function of the impedance of the EKG amplifier.

The underlying theory of the invention is that the heart acts as a battery. A battery fails when its internal resistance has increased to a level at which the battery can no longer supply a useful amount of power to an external load. That same principle applies to the measurement of electrical energy generated by the heart. That is, if several loads are applied to the measurement device, which may be an implantable cardiac pacemaker, a defibrillator, a device for monitoring the occurrence of heart failure, or a diagnostic device for monitoring the physical condition of a patient, the same phenomena can be used to calculate the internal impedance at the site of measurement. Preferably, the calculation or determination is of the thoracic (and preferably, intrathoracic) impedance or of local impedance and/or its relative changes with time for a given patient.

According to an important aspect of the invention, a method of evaluating the cardio-circulatory condition of a patient would include determining the patient's thoracic impedance based on information solely derived from the electrical energy generated by the patient's own heart. The intrathoracic impedance information may be used, for example, to optimize the rate response of a rate adaptive pacemaker, or to optimize monitoring of the patient's congestive heart failure. Another aspect of the invention, then, may be characterized as a method of adjusting the heart rate of a patient by means of an implanted rate adaptive pacemaker, where automatic adjustment of the pacing rate of the pacemaker is achieved in response to a determination of the patient's intrinsic impedance derived solely from the electrical energy generated by the patient's heart. The patient's intrinsic impedance information may be used instantaneously to influence the rate adaptation on a continuous or ongoing basis within minutes. Alternatively, the rate and cardiopulmonary response derived from the intrinsic impedance may be applied to determine the rate adaptation on a longer term basis, such as on a daily or monthly basis.

It is therefore another important aim of the invention to provide a system which uses an impedance derived parameter, such as ventilation, as a closed loop parameter to optimize the rate response of an implantable rate adaptive cardiac pacemaker or defibrillator.

The invention may be further stated as allowing the cardiopulmonary status of a patient to be monitored with an implantable monitoring device, by calculating the patient's thoracic impedance based on information derived from the electrical energy generated by the patient's own heart. For example, the device may be implanted subcutaneously to monitor the patient's EKG, and to detect changes in the thoracic impedance based on differential signal processing of the EKG. Then, information concerning the impedance changes may be applied within the device to determine the cardiopulmonary status of the patient. In circumstances where the patient is suffering from heart failure, the device is adapted to monitor the patient's heart failure by performing the calculation of impedance and processing thereof solely using the electrical energy generated by the patient's own heart.

Information about the cardiac function of the patient may be obtained using a method according to the invention, in which electrical signal information from an EKG derived from depolarization and repolarization of the patient's heart, representing systole and diastole, accordingly for different phases of the heart represented by the EKG, is continuously processed using electrical energy generated by the patient's own heart. On the other hand, the impedance of the patient's heart may be analyzed with systole h m a point close to the T-Wave of the EKG signal, and information on the diastolic status of the heart may be derived from an impedance signal at the R-Wave of the EKG signal. Then, a comparison between systole and diastole may be used to ascertain indirectly cardiac stroke volume and the cardio-pulmonary status of the patient.

Similarly, the function of a body-implantable defibrillator may be enhanced according to the invention by determining the impedance between sensing electrodes of the defibrillator, and determining changes in that impedance based solely on energy generated by the patient's heart.

It will be seen from the ensuing detailed description that a device for evaluating the cardio-circulatory condition of a patient is implemented with means for determining the patient's thoracic impedance and impedance changes based on information solely derived from the electrical energy generated by the patient's own heart. And the desired information may be obtained by extremely simple means so that the changes or additions required to achieve these benefits with even currently available devices can be minimal, such as including surface mounted electrodes for monitoring the patient's surface EKG in subcutaneously implanted devices.

DRAWINGS

The above and other aims, objectives, aspects, features and advantages of the invention will be better understood from a consideration of the following detailed description of the best mode contemplated for practicing the invention, taken with reference to certain preferred implementations and methods, and the accompanying drawings in which:

FIG. 1A-1D are schematic diagrams of an electrical circuit or system in which a patient's heart is represented by an internal resistance, useful for explaining the basic principle of the present invention;

FIG. 2 applies the concepts discussed with reference to FIG. 1, to the principle of different EKG vectors, FIG. 2A illustrating EKG vectors measured for a patient, and FIG. 2B illustrating the EKG tracings for different placements of EKG electrodes;

DESCRIPTION

Figure 2B:
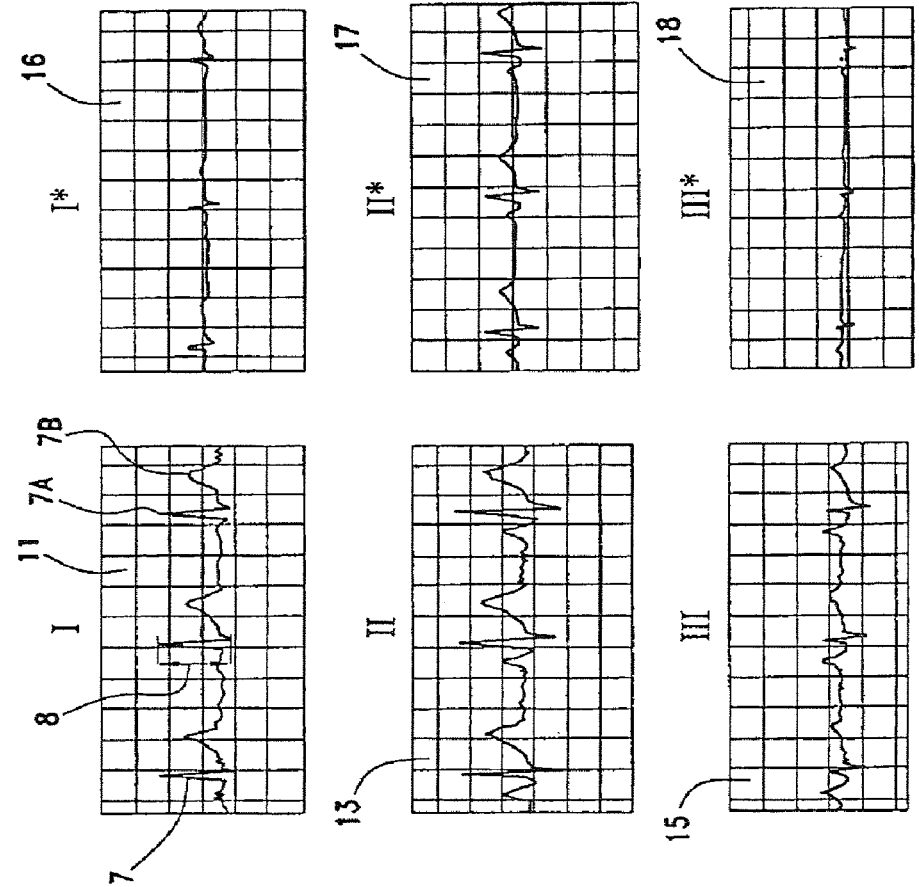

The entire content of U.S. application Ser. No. 11/104,389 filed Apr. 11, 2005, U.S. application Ser. No. 10/622,184 filed Jul. 16, 2003, U.S. application Ser. No. 10/155,771, filed May 25, 2002, now U.S. Pat. No. 6,829,503, and DE 10148440-2, filed Oct. 1, 2001, are hereby incorporated by reference.

The method and device of the invention will be better understood by reference to a presently preferred embodiment constituting a standalone diagnostic or therapeutic device to enhance the specificity of a body-implantable device such as an artificial cardiac pacemaker, a defibrillator, a cardiac resynchronization device, or a monitoring device for evaluating the cardiopulmonary functional status of the patient.

Throughout the views of the drawings, identical reference numbers indicate identical structures. Views of the device or the method either alone or implanted are not intended to represent the actual or relative sizes or rather give principle understanding of the methods and devices.

FIGS. 1A-1D are simplified schematic diagrams of an electrical circuit or system in which the heart of a patient 1 is represented by an internal resistance $R_{internal}$ 2, at least in parts 1A and 1B. In principle, $R_{internal}$ is the sum of many individual resistances or impedances consisting of myocardial tissue, fibrous connective tissue in the heart, pericardium, blood within the heart, fluids within the intracellular spaces, and the surrounding environment of connective tissue atria, pulmonary structures, venous structures, and lung tissue. The multiplicity of cells within the heart depolarize, and this depolarization creates an electrical force which threads through the heart with a certain vector. This initial electrical source represented in the circuit schematic of the Figures as a voltage source E (3) has a magnitude that can be measured between electrodes at points A (4) and B (5). The latter two points may constitute the sites of electrodes of an external measuring instrument or EKG amplifier.

Virtually the same voltage as the original source voltage E 3 will be present and remain so, if the impedance between measuring points 4 and 5 has a magnitude of several megohms. This is because under that condition little or no current is flowing between those points. In principle, this maximum voltage is present, for example, at the input amplifier of an implantable pacemaker, since they have an impedance of several hundred kilohms or megohms; and the same is true of other implantable diagnostic devices, such as devices that measure the patient's EKG. For example, external EKG strip chart recorders or EKG monitors have an impedance of 1 megohm or more, thereby allowing them to detect the maximum voltage present between points of the body at which their electrodes are attached or located.

In FIG. 1B the schematic shows a heart 1, in circuit with an internal resistance 2, a source voltage 3 that is detected between electrode points or sites 4 and 5, corresponding to what has been described above for FIG. 1A. However, in this case an additional external resistance of magnitude $R_{Load}$ 6 is connected in circuit between electrode points 4 and 5. If the magnitude of the resistance of load 6 is considerably lower than the input impedance between 4 and 5 represented by, say, the virtual open circuit impedance of an amplifier, discussed for the circuit of FIG. 1A, considerable current will be shunted through this lower resistance. As in the case of a failing battery, then, the initial full voltage E (3) will not be detected since, by Ohm's Law (U=IR), a drop in voltage will be observed with decreased R.

This example is carried forward in FIGS. 1C and 1D. In each of those Figures, the heart 1 generates a certain EKG signal 7 between measuring points 4 and 5, which has a certain amplitude 8. In FIG. 1D, the connection of an input amplifier 8 with a relatively low resistance 6 across points A and B results in an EKG signal 7 having an amplitude considerably lower than that in the case of the much higher, virtually open circuit resistance across A and B in FIG. 1C.

In principle this observation can be compared to a battery. When a battery fails it is typically because its internal resistance has increased to a level that no longer supports the supply of a useful amount of electrical energy to an external load. If one measures the voltage V of a failing battery which is disconnected, it is usually found that the battery has a nearly normal voltage because a conventional voltmeter used to perform the measurement has an input resistance much higher than the internal resistance of the battery. If, however, the failing battery is connected to a low external resistance such as load 6 in FIG. 1B, the terminal voltage U of the battery drops precipitously. This can be interpreted as the battery dropping most if its source voltage across its own internal resistance, so little or no voltage is available for external services. For example, an ideal battery with 0 internal resistance or infinite internal conductance and a voltage E of 12 volts, when supplying power to an external load having a resistance of 1 ohm, will produce a current of I=12 amps and a power of E×I=144 watts. If the battery has an internal resistance of 2 ohm, or an internal conductance as low as 0.5 siemens, then with this load, the terminal voltage U of the battery will drop to 4 volts. The output current of this failing battery will drop to $I=U/R_{load}$ which is 4 amps, and the output power is 16 watts.

The same principle holds for conventional electrocardiography along the main electrical excitation vector. Since an EKG measurement is detected with high input impedance, this conventional measurement gives no insight into the electrical power of the source, in this case the heart of the patient. Furthermore, the absolute voltage of EKG signals is not a valuable indicator of various pathological situations. Indeed, despite great diversity of cardiac diseases, it is common clinical experience that individual variability and the amplitude of the EKG wave as detected from state of the art EKG amplifiers is not indicative of any kind of disease. The voltage of a conventional EKG is reduced only in very few clinical situations when large electrical shunts are present, such as a pericardial effusion which constitutes a large conductor around the heart that shunts the electrical energy with low intrinsic resistance.

The terminal voltage U in FIG. 1B (which represents the R wave amplitude 8, represented in FIG. 1C by QRS-complex 7) should drop by $E-(R_{internal} \times I)$, where $I=U/R_{Load}$. The internal resistance $R_{internal}$ 2 can be calculated by the equation $R_{internal}=(V-U)/(U/R_{Load})$, where V is the voltage between electrode points 4 and 5 which is disconnected from the load in FIGS. 1A and U is the terminal voltage between 4 and 5, across which the electrical load $R_{Load}$ 6 is connected. Based on $R_{internal}$, the internal electrical conductance $S_{internal}$ of the heart can also be calculated by the equation:

$$S_{internal}=1/R_{internal}, \text{ in siemens.}$$

Figure 2A:
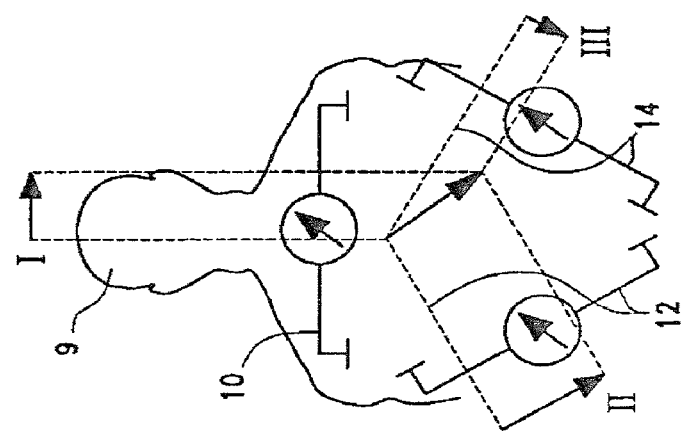

These equations are applied in practice in FIG. 2, according to the principle of different EKG vectors. FIG. 2A represents a patient 9 in which EKG lead 110 is represented by electrodes to the patient's right and left arms, with voltage measurements shown in EKG tracing 11 (FIG. 2B). Electrode detection lead/electrodes II 12 produces the tracing 13, and the voltage detected between the electrodes of lead III 14 is shown in the tracing 15 for lead III. Tracings 11, 13, and 15, then, represent the EKG signal obtained for the respective vector projections of the leads 10, 12 and 14. If an external load is now connected in parallel with the input impedance of the EKG amplifier, a voltage drop will be observed for the same patient as shown by tracings 16 (for lead I), 17 (for lead II), and 18 (for lead III), because part of the energy delivered from the patient's heart is shunted through the additional external load.

FIG. 3 illustrates various situations in which the internal resistance $R_{internal}$ of the heart is represented not as one single value, but by plural individual impedances. In FIG. 3A, the internal resistance $R_{heart}$ of the heart 19 is represented by the structural resistance of the heart made up of cells, connective tissue, and primarily solids, and a variable component of resistance $R_{inspiration}$ (or $R_{insp}$) 20 is primarily represented by the filling of the heart with blood. Since blood has a specific impedance of roughly 50 ohms per centimeter (cm), while the specific impedance of heart 19 is 400 ohms per cm, there exists a great influence on the total impedance of the heart, because these two components are in parallel. The internal voltage source 3 in FIG. 3A detected between electrode points 4 and 5 represents a voltage $V_1$ (22) that equals primarily E 3 if the input impedance between 4 and 5 is sufficiently high that all of the voltage E drop occurs between 4 and 5.

Figure 3A:
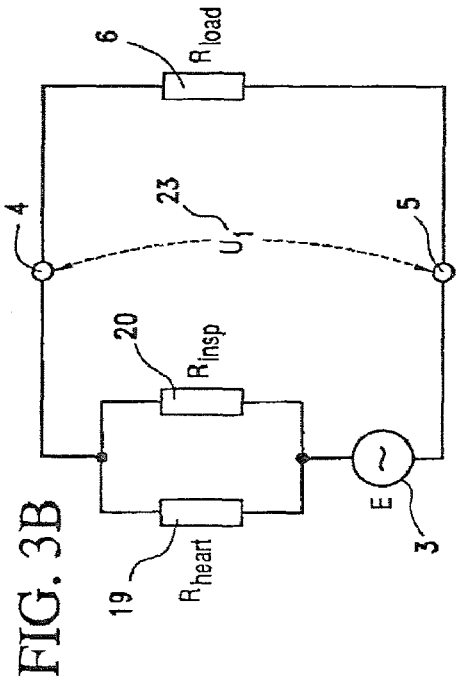
FIG. 3 illustrates various situations in which the internal resistance of a patient's heart is represented in parts A, By C and D not as one single value, but by plural individual impedances.
Figure 3C:
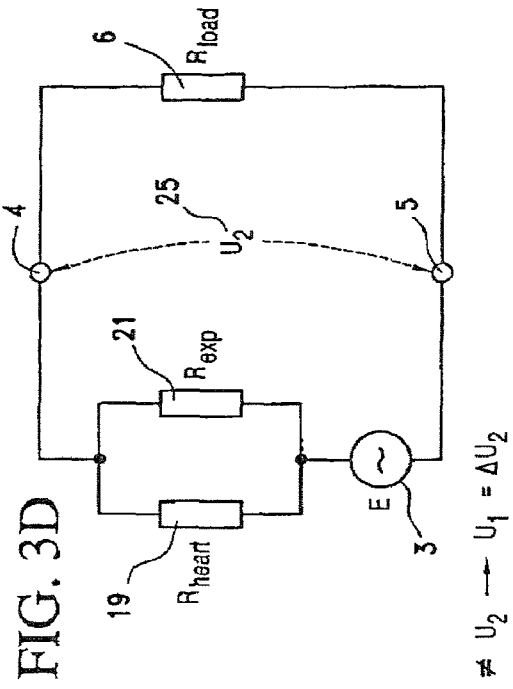
Figure 3B:
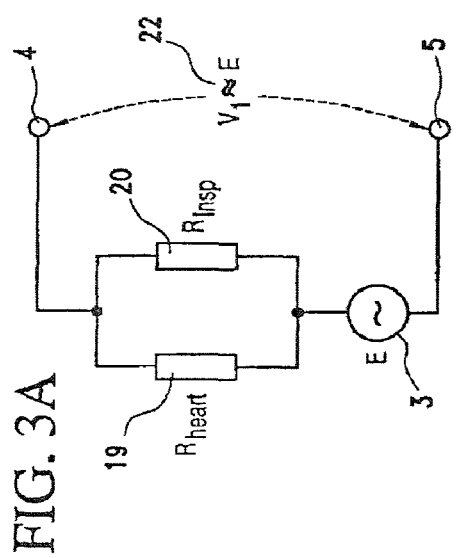
Figure 3D:
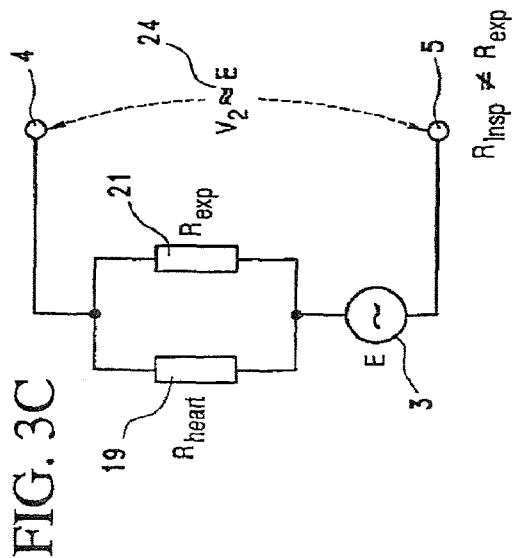

If, however, an additional external load $R_{load}$ 6 of roughly 1 kilohm or less is applied as shown in FIG. 3B, then the voltage between 4 and 5 drops to a voltage U1 (23) which, as earlier described, is lower than the voltage E 22. FIG. 3C illustrates the situation in which a variation now occurs in internal resistance 21, representing the resistance with expiration ($R_{expiration}$ or $R_{exp}$). The total voltage to be detected $V_2$ 24 is now primarily composed of the parallel resistances of $R_{heart}$ 19 and $R_{exp}$ 21. A variation between $R_{insp}$ 20 and $R_{exp}$ 21 will not affect the resulting voltages, $V_2$ 24 or $V_1$ 22, since the input impedance between electrodes 4 and 5 is sufficiently high to avoid further voltage shunting and voltage drop. However, as shown in FIG. 3D, the external load 6 will affect voltage $U_2$ 25 with a variation in internal impedance 21 during expiration, compared to impedance component 20 during inspiration. Thus, if an external load 6 of sufficient load resistance, such as 1 kilohm, is applied to a primarily high input impedance amplifier, variations in internal total resistance build up from $R_{heart}$ 19 and 20 or 21 have a much greater effect on voltage $U_1$ 23 with inspiration and $U_2$ 25 with expiration. In principle, for this condition it can be said that $R_{inspiration}$ is not identical with $R_{expiration}$, and therefore, $U_1$ 23 is different from $U_2$ 25. It follows that $U_1$ equals the delta of $U_2$, and this represents more or less the impedance factor of respiration, the term "impedance factor" meaning the quotient of impedances 19 and 20 in FIG. 3B compared to the impedances 19 and 21 in FIG. 3D.

Figure 4:
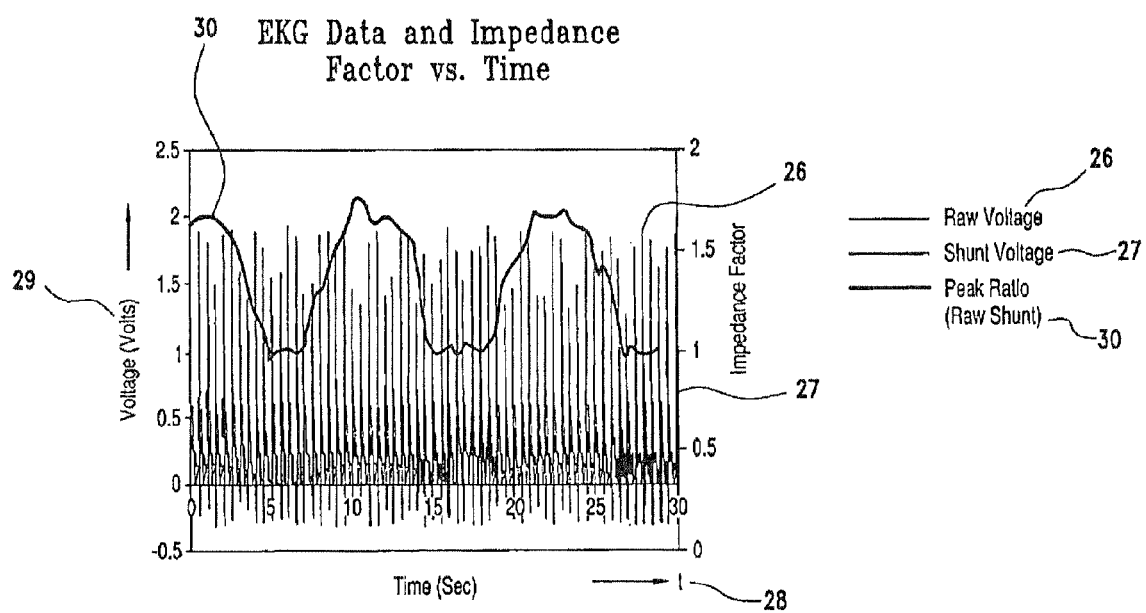
FIG. 4 is a graph of EKG data and impedance factor versus time that illustrates results from measurements taken with an intracardiac electrode.

FIG. 4 is a graph of EKG data and impedance factor versus time that illustrates results from measurements taken with an intracardiac electrode. A bipolar conventional pacemaker electrode was implanted in the heart and measurements were taken between the electrode tip in connection with the myocardium and a ring located roughly 1 cm behind the electrode tip. These sites can be considered as electrode points 4 and 5 in the Figures described thus far, and a linear high quality amplifier was connected between these two sites. The signal processing was performed in such a way that one signal represented in FIG. 4 as raw voltage 26 represented by the higher bars in the graph was compared to a shunt voltage 27 represented by the smaller bars. To detect the shunt voltage from the same electrode site 4 and 5 by a special program, the input impedance was shunted by a resistance of one kilohm. In FIG. 4 the time axis (abscissa) 28 shows increments of time in seconds and the voltage axis (left ordinate) 29 shows increments of the detected voltage of the two signals raw voltage 26 and shunt voltage 27. The curve 30 represents the quotient between voltage 26 and voltage 27 (i.e., their impedance factor, measured along lines parallel to the right ordinate) or in other words, the quotient of the impedances that change with respiration.

As is clearly seen in the graph, the ratio of the peak signal between raw voltage 26 and shunt voltage 27 represented by curve 30 correlates with the respiration, which was set to 5.5 cycles per minute. The time interval for one respiratory cycle is 11 seconds in this example, which actually represents a ventilation rate of 5.5 cycles per minute.

Various aspects of the continuous EKG signal can be used to derive measurements of impedance factor in FIG. 4, to discern or determine the cardio-pulmonary status of the patient using, in this example, the bipolar conventional pacemaker electrode implanted in the heart for monitoring purposes. Either a continuous line can be averaged if a sufficiently high digitization rate is applied, or, to simplify measurements and procedures, and also to facilitate data handling and power consumption in an implantable device, only certain aspects of the EKG signal need be taken. For example, the latter aspects may be those represented previously herein in EKG signal 7 with amplitude 8, so it is feasible to use only the peak 7A of the R Wave or to take other aspects such as only or additionally the T-Wave peak 7B, of the EKG signal 7 illustrated in FIG. 2B. In the example shown in FIG. 4, the peak of the R-Wave was applied. From the latter Figure, it is clear that considerable variation occurs in the quotient represented by curve 30 (the impedance factor) between inspiration and expiration, which corresponds to the ventilatory cycle rate and its amplitude.

Figure 5:
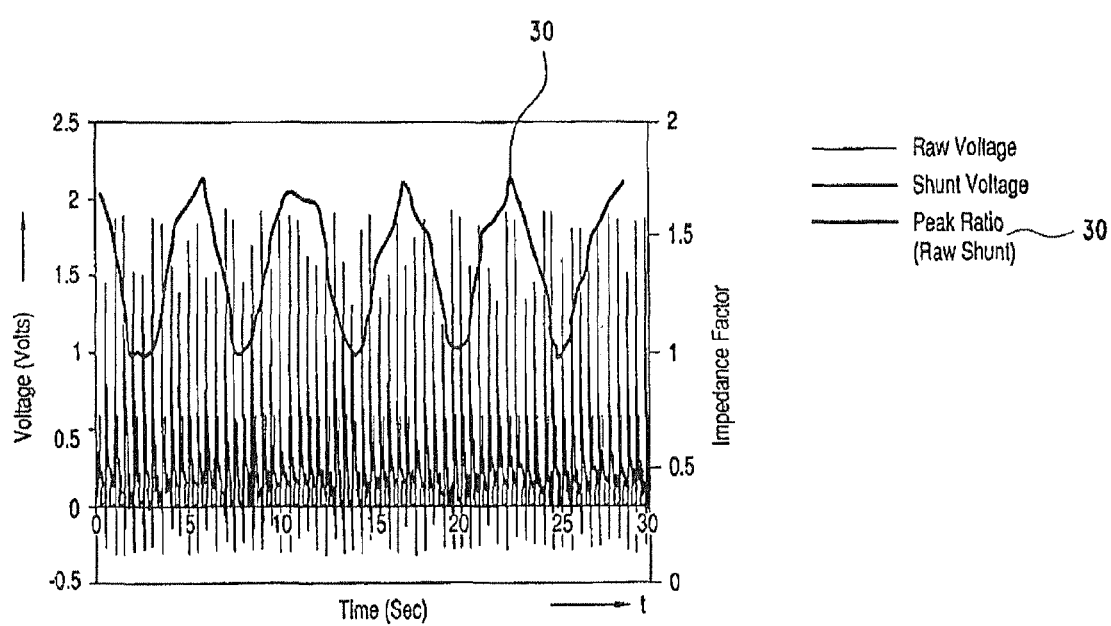
FIGS. 5 and 6 are graphs of EKG data and impedance factor vs. time corresponding to FIG. 4, except for changes (respective increases) in the respiratory rate.
Figure 6:
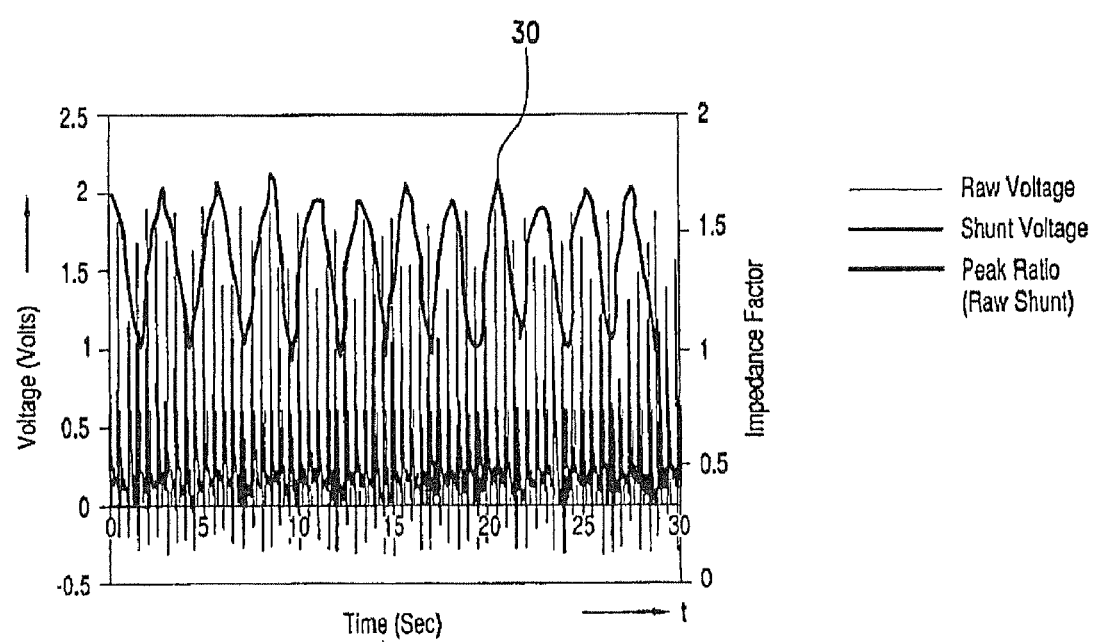

FIGS. 5 and 6 are graphs illustrating the same data setting and the same parameters as in FIG. 4; however, the respiratory rate was changed in FIG. 5 to 10 cycles, and in FIG. 6 to 20 cycles per minute. This change in frequency is clearly shown in the latter two Figures, being represented by peak ratio 30.

Figure 7:
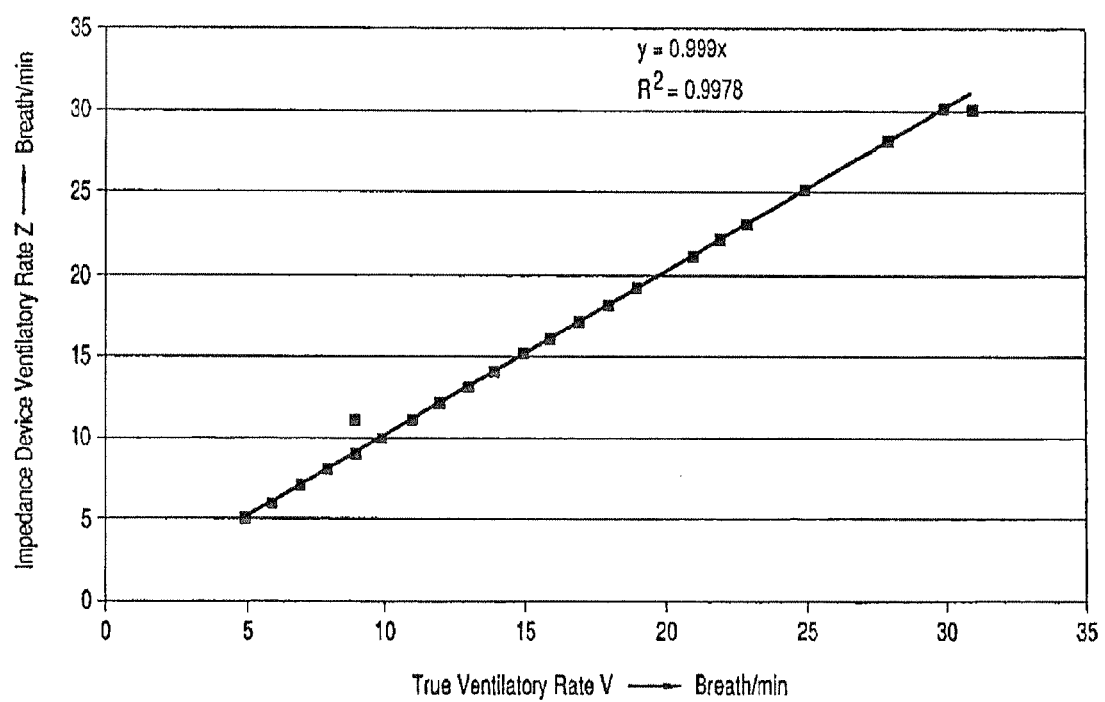
FIG. 7 is a graph that summarizes and compares the measurements of impedance derived ventilatory rate obtained using two different methods.

FIG. 7 is a graph that summarizes and compares the measurements of true ventilatory rate V along the abscissa and of the impedance factor derived ventilatory rate Z along the ordinate. As shown, there is nearly a 1:1 correlation between the two methods which means that ventilation can be truly detected, as far as the frequency of breaths is concerned, from the impedance derived signal in which the heart serves as the power source for the impedance calculation.

Figure 8:
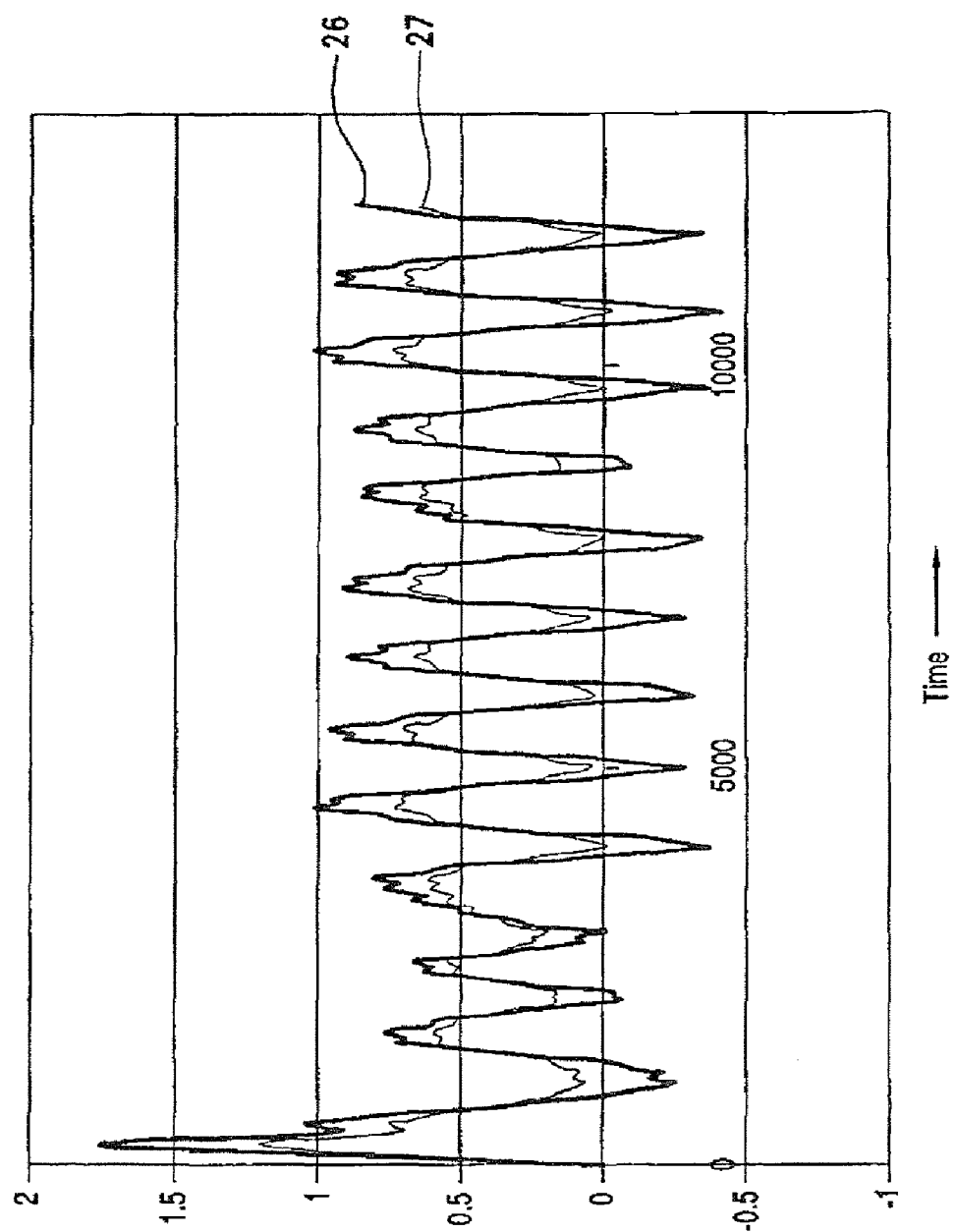
FIG. 8 is a graph that depicts a preferred application of the signal processing means, with relative signal amplitudes over time.

FIG. 8 depicts a preferred application of the signal processing means, with the abscissa showing units of time and the ordinate showing the signal amplitudes of the raw voltage 26 and the shunt voltage 27 relative to one another. The former is indicated by the higher amplitude and the latter, derived from the shunted input impedance which was reduced to 0.5 kilohm, is indicated by a lower amplitude. The signal processing of both signals 26 and 27 included passage through a low pass filter for smoothing.

The application of low pass and high pass filtering in the signal processing can be performed by either a conventional analog technique or also by conventional digital technique of first, second, third or fourth order. The selection of the cut off frequency depends on preference as to which signal components should be detected. If it is preferred to detect respiration and respiration rate by filtering with a cut off frequency below twice the maximum frequency that is expected. For most patients, a respiratory rate of no more than 50 breaths per minute can be expected, which means that a low pass filter of about 1.5 Hz or less will allow detecting the respiratory rate. In FIG. 8 the difference in signal amplitude between signal 26, which was detected from input impedance of more than 1 megohm, and signal 27 detected from an input impedance of 0.5 kilohm, becomes evident from FIG. 8. The respiratory cycle rate is also evident.

Figure 9:
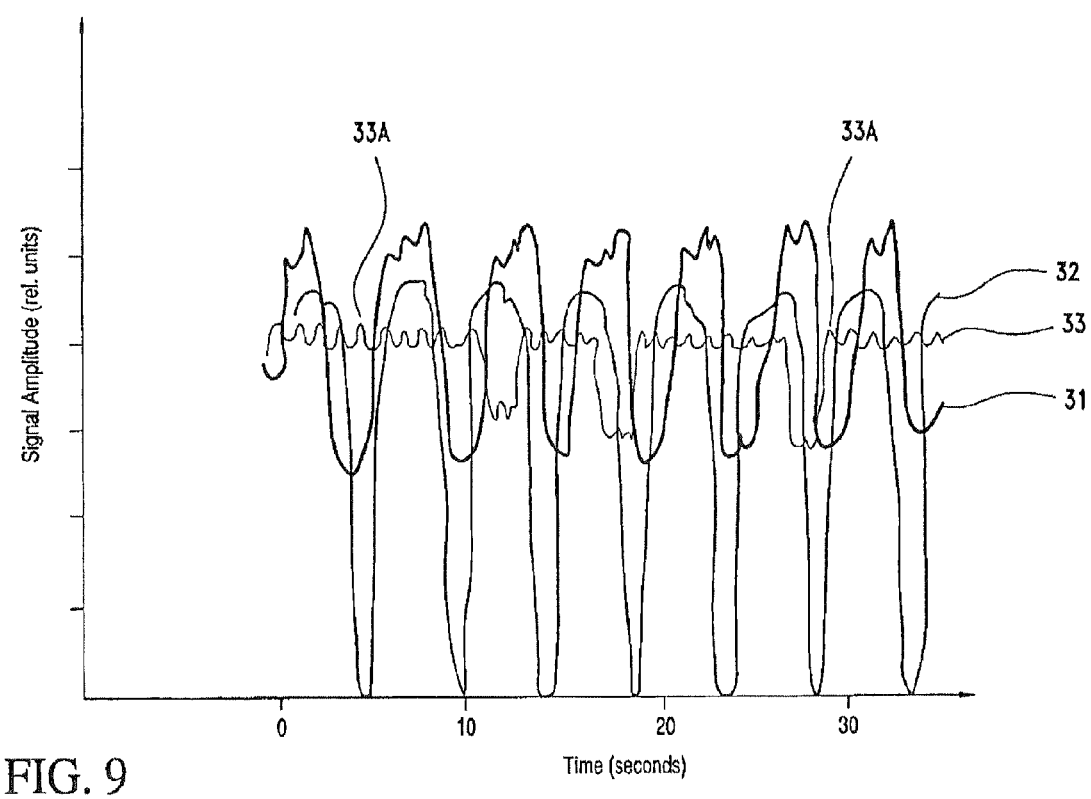
FIG. 9 is a graph that represents the quotient of raw voltage and shunt voltage with different depth and modes of breathing.

FIG. 9 is a graph that represents the quotient of raw voltage and shunt voltage with different depths or amplitudes and modes of breathing. This graph shows that it is not only feasible to detect respiratory rate, which is effected by change in the filling of the heart with blood and by a volume change of the amount of blood surrounding an electrode implanted in the heart with a conductor such as blood, but it is also feasible to detect a relative change in amplitude following different tidal volumes. Graph 31 represents the signal derived from the impedance quotient of high input impedance of more than 1 megohm and 1 kilohm with external artificial ventilation of an individual with a tidal volume of 300 ml per breath. Line 32 shows the same for a tidal volume of 850 ml. Line 33 depicts the impedance quotient with spontaneous breathing at a considerably lower rate. Now the signal shows not only the breathing or ventilation, but also the cardiac component 33A indirectly reflecting stroke volume with systole and diastole. In order to obtain this, for example, one need only observe the depolarization that occurs with the electrical signal represented by the peak of the R wave 7A in the EKG or relative to the repolarization that occurs with the peak of the T wave 7B, recognizing that the mechanical contraction occurs slightly after the peak of the R wave. At this point, intracardiac impedance allows determining the extent of filling of the heart and to derive therefrom indications of heart failure.

Figure 10:
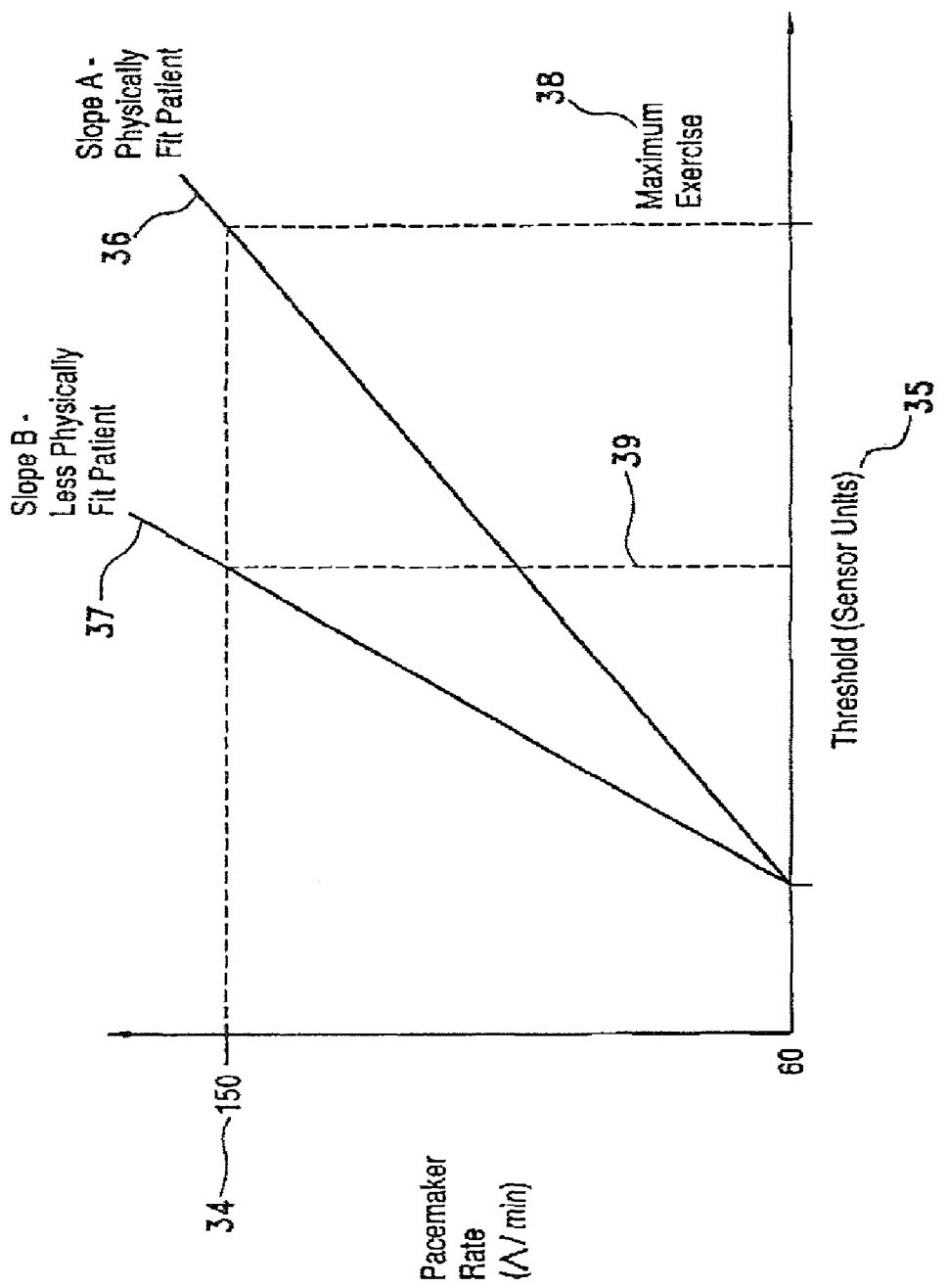
FIG. 10 is a graph that depicts adjustment of pacing rate, in units of pacing rate versus extent of a patient's physical activity detected by a sensor; for rate responsive pacing.

FIG. 10 is a graph that depicts, in units of pacing rate versus extent of physical activity detected by a sensor, the principle currently used for rate responsive (or rate adaptive) pacing in cardiac pacemakers and in defibrillators, to adjust the heart rate or the pacing rate of a patient based on the input received from a sensor (such as an accelerometer in heretofore available devices). In the Figure, sensor units 35, which may, for example, be activity counters, amplitude of an activity signal, or any other physiological parameter which has a correlation to heart rate in healthy persons such as body temperature, ventilation, or mechanical forces acting on the body. These units are translated in a slope function into a rate response with more sensor units yielding a high pacemaker rate 34. Based on empirical assumptions a certain slope is selected for a given patient. Slope A (36) represents a correlation of sensor units and pacemaker rate for a physically fit patient, while a slope B (37) is selected for a less physical patient. On average, there is a threshold on which the heart rate is increased until maximum exertion 38 and maximum heart rate 34 are reached.

The limitation with all these open loop systems of the prior art is that the slope that sets an individual rate with a given exercise is selected on an empirical basis; however, it is not confirmed that this heart rate is the optimum heart rate for the given situation of a patient. Even in the same patient, the most beneficial rate with a given exercise might change from day to day. Some patients have significant coronary heart disease which limits the flow of blood through the coronary arteries and therefore induces an ischemia. Therefore, it is sometimes beneficial to limit the maximum heart rate and the slope to different values (e.g., 39) compared to a state that might have been present weeks or even only days ago when the myocardial perfusion was different. The lack of a feedback parameter is one of the limitations of currently widespread use of rate adaptive pacemakers.

Considering the limitation of currently open loop rate regulation implantable pace makers, an impedance derived parameter according to the invention can be used not only to adjust the pacing rate directly so as to create a correlation between signal and pacing rate on a linear or nonlinear basis as has been suggested in the past by ventilation control rate adaptive pacemakers, but it also can be used to control the individually optimum pacing and heart rate on a closed loop basis, and also on a long term trend basis. In the past it has been considered that hemodynamic parameters would be suitable for a closed loop system. However, the limitation is to derive hemodynamic parameters directly. The complexity and change in those parameters and the technical difficulty to measure an actual derivative of cardiac output or stroke volume has prevented an introduction of those practices into clinical practice. In stark contrast, the present invention provides a novel minimally energy demanding system that allows controlling the effect of pacing rate and the adequacy of pacing rate by monitoring the ventilation and/or cardiac parameters derived from an impedance signal which is obtained in a manner according to the invention.

Figure 11:
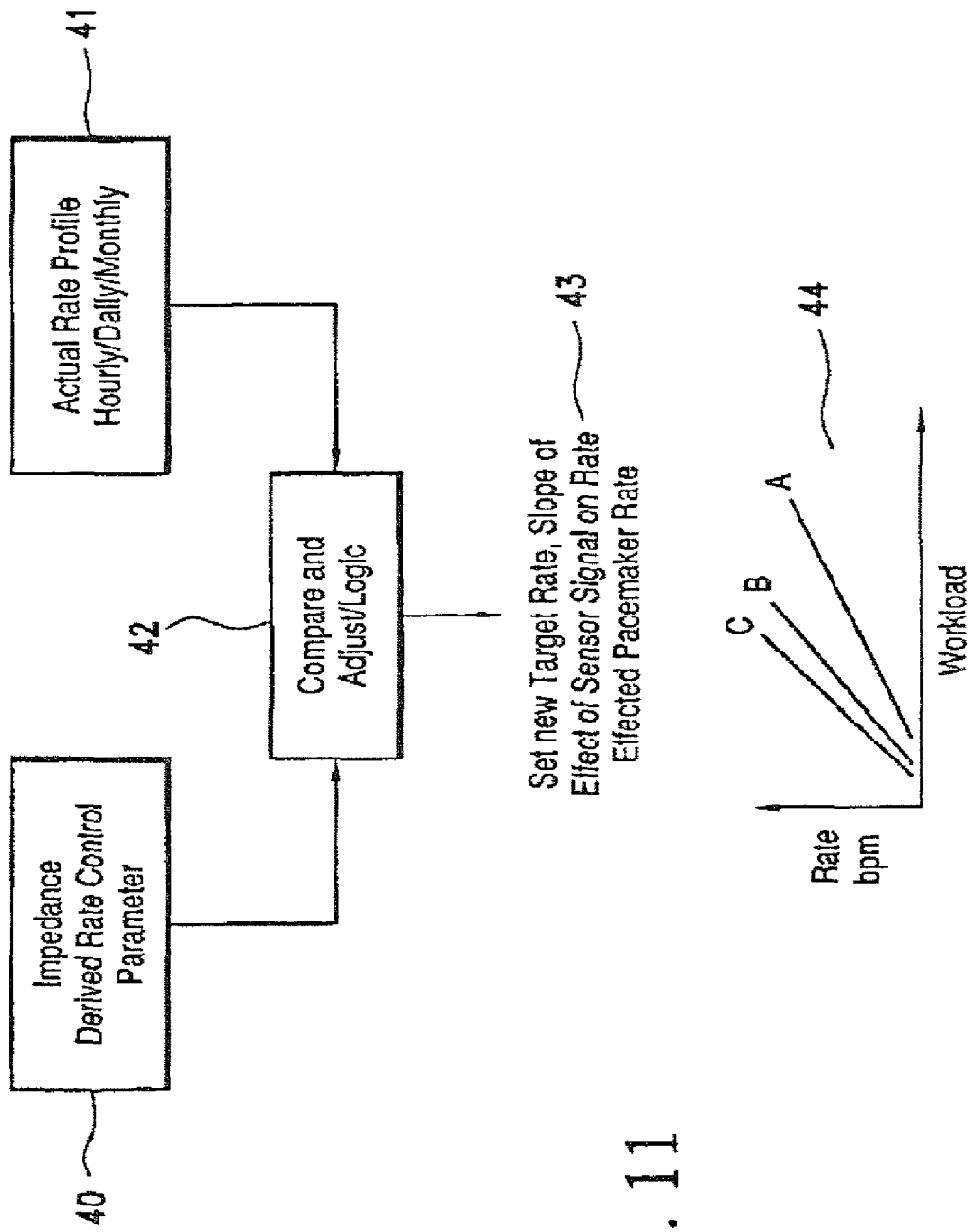
FIG. 11 is a flow chart that shows the principle of a closed loop rate profile optimization.

FIG. 11 is a flow chart that shows the principle of a closed loop rate profile optimization. In this optimization, the impedance derived rate controlled parameter is processed and stored in circuitry 40 which would process the signals obtained and store them in a conventional memory means of an implantable device such as an implantable pacemaker or defibrillator. This can be done either as a long term average over several days, or over a shorter term average over a daily or even an hourly or minute-by-minute basis. The difference between long term and short term averages as described in previous patents by the applicants referenced earlier herein may be applied to this process. The actual rate profile is available from the second circuitry 41. This actual rate profile is compared to the long term impedance derived rate control parameter in a comparator and logic circuit 42, and the output is used to adjust the heart rate setting at 43. This not only controls the slope, for the correlation of pacing rate to a given signal intensity or work load as shown in the graph 44, but may also be used to set a new target rate and base rate. In this way, an optimization of the rate profile and slope can be achieved by means of minimal additional hardware complexities, since the EKG electrodes, the EKG amplifier and the information is already available to any demand pacemaker and defibrillator.

Alternatively, the signal can be also processed on a short-term, so that the effect of the heart rate adjustment can be evaluated against the ventilation and cardiac response within tens of seconds to achieve an individual optimization by circuitry 42. The pacing rate that gives the lowest ventilation response is the optimum for a given work load. It is known that a person who cannot increase his heart rate will breathe more heavily than one who has the more adequate heart rate. Experiments done by the applicants have shown in the past that if the pacing rate is kept constant at 70 bpm and there is no further rate increase with exercise, the exercise capacity of a patient is limited and he/she will breathe heavily despite the limited exercise capacity. Therefore, the response of ventilation can be taken as an indirect indicator of the metabolic load and of the efficiency of the cardiocirculatory system. In this way, the invention fulfills an aim to provide a system that uses ventilation as a closed loop parameter to optimize the rate response given brought forward by a different sense of parameter. In addition, ventilation can also be used as a primary parameter to adjust the heart rate with or without secondary optimization provided through another sense parameter.

Figure 12:
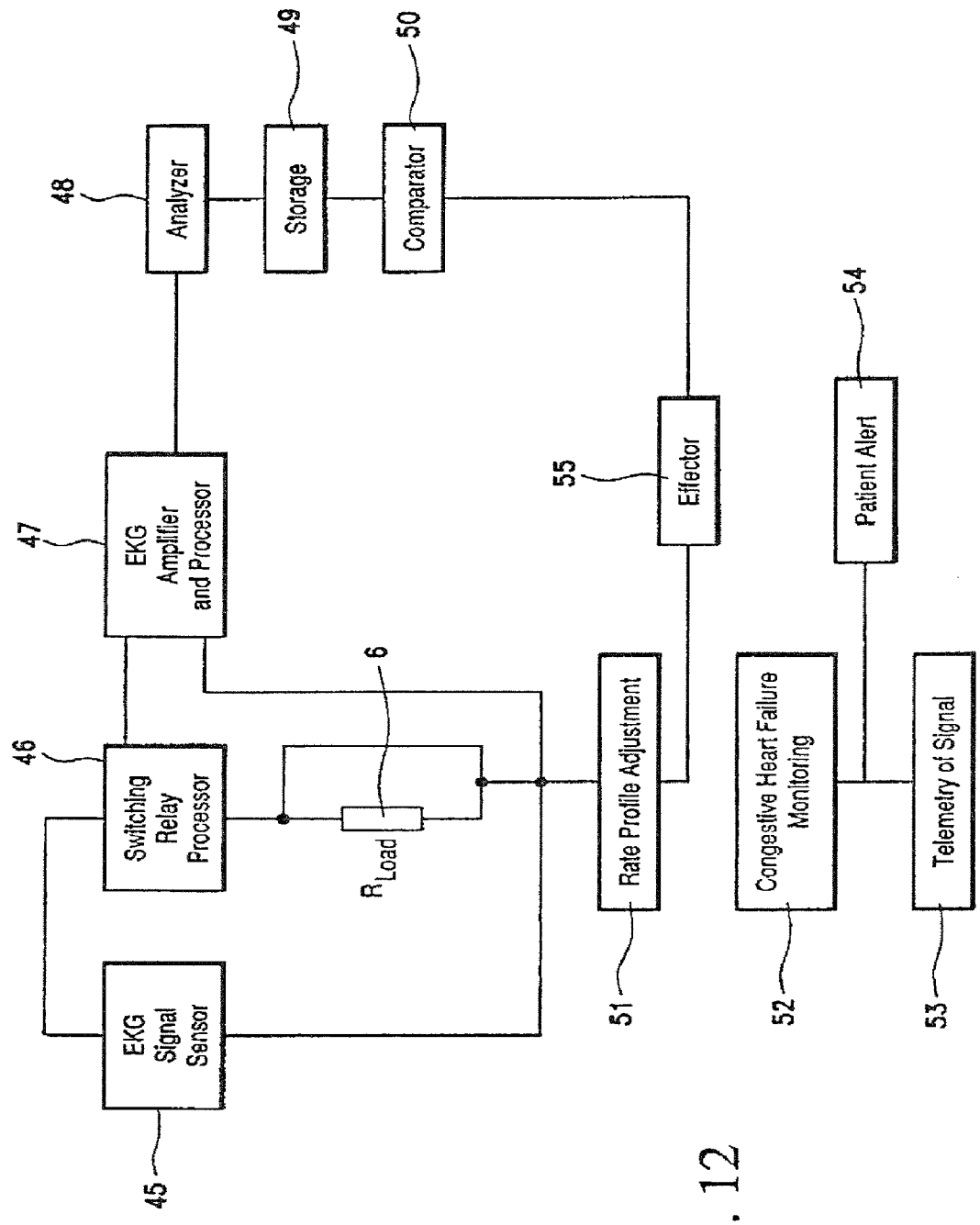
FIG. 12 is a flow diagram of the principles and signal processing of the present invention.

FIG. 12 is a flow diagram of the principles and signal processing of the present invention. An EKG signal sensor 45 consists of electronic means that makes connection with the site where the EKG signal is sensed either merely on an intracardiac basis, from a bipolar electrode, from a unipolar electrode (one electrode in the heart and one on the case), or from separate electrodes on an implantable case such as surface-mounted electrodes on a pacemaker, a defibrillator, or monitoring device that is preferably implanted subcutaneously, or implanted in a different location in the body as described in the cross-referenced related applications. At least bipolar EKG signals are sensed, and by a switching relay process 46 a load 6 is either added or not added to the signal circuitry. Thereby, two different EKG derived information signals are available for EKG amplifier and processor 47, one signal with and one signal without the load. Comparator and analyzer 48 derive the desired information from the quotient of the two impedances that correspond to voltages and impedances derived from a high and a low input impedance. This information is then provided on either a filtered or processed basis to storage medium 49 in which several long term, short term, and derivatives of the signals can be stored. Comparator 50 finally derives the information that is required to the respective implantable device either for a rate profile adjustment and optimization 51, or if it is only for monitoring purposes, for congestive heart failure 52 as described as one of exemplary embodiments in the aforementioned related '184 patent application. This telemonitoring signal can be telemetered to an outside device or through telemetry 53 or can also provide patient alert 54 in case of detecting a deviation from the desired pattern for the individual patient. Electronic means applied are state of the art, with switching relay process, EKG signal sensor, amplifier processor, analyzer, storage and comparator provided either in a single chip or the like, or in conventional electronic components applying a combination of digital and analog techniques or in solely digital techniques including filtering and effector 55 that converts the available information into the desired action within the device.

In summary, the current invention provides a facilitated monitoring means to optimize both therapeutic and diagnostic capacity of an implantable device by means of impedance derived information, and to acquire this information using the patient's own heart to provide the necessary electrical energy.

Although a presently contemplated best mode of practicing the invention has been disclosed by reference to certain preferred methods, it will be apparent to those skilled in the art from a consideration of the foregoing description that variations and modifications may be made without departing from the spirit and scope of the invention. Accordingly, it is intended that the invention shall be limited only by the appended claims and the rules and principles of applicable law.

What is claimed is:

1. A machine-implemented method of evaluating the cardio-circulatory and ventilatory condition of a patient, which comprises the steps of:
    determining the patient's thoracic impedance based on information solely derived from the electrical energy generated by the patient's own heart; and
    evaluating the cardio-circulatory and ventilatory condition of the patient based on patient's thoracic impedance.

2. The method of claim 1, including using the patient's thoracic impedance information to optimize the function of a rate adaptive pacemaker.

3. The method of claim 1, including using the patient's thoracic impedance information to optimize monitoring of the patient's congestive heart failure.

4. A machine-implemented method of adjusting the heart rate of a patient by means of an implantable rate adaptive pacemaker, said method comprising the steps of:
    determining the patient's intrinsic impedance based on information derived solely from the electrical energy generated by the patient's heart; and
    adjusting the heart rate of the patient by adjusting said pacing rate of said implantable rate adaptive pacemaker based on the patient's intrinsic impedance.

5. The method of claim 4, wherein said adjusting step comprises closed loop optimization of said rate adaptive pacemaker to achieve said adjustment of pacing rate.

6. The method of claim 4, including using the patient's intrinsic impedance information to adapt the heart rate of a rate adaptive pacemaker accordingly.

7. The method of claim 4, including using the patient's intrinsic impedance information instantaneously to influence the rate adaptation on an ongoing basis within minutes.

8. The method of claim 4, including using the patient's intrinsic impedance information in which long term rate and cardio-circulatory response determine the rate adaptation on a long term daily or monthly basis.

9. A machine-implemented method of monitoring the cardiocirculatory status of a patient with an implantable device, said method comprising the steps of:
    calculating the patient's impedance based on information derived from the electrical energy generated by the patient's own heart; and
    monitoring the cardiocirculatory status of said patient based on the patient's impedance.

10. The method of claim 9, wherein said implantable device is implanted subcutaneously.

11. The method of claim 9, wherein said device is adapted to monitor the patient's EKG, and including the step of deriving changes in said impedance based on differential signal processing of said EKG.

12. The method of claim 11, including the step of applying information concerning said impedance changes within said device to determine the cardiocirculatory status of the patient.

13. The method of claim 9, wherein the patient is suffering from heart failure, and said device is adapted to monitor the patient's heart failure by performing said calculation of impedance and processing thereof solely using said electrical energy generated by the patient's own heart.

14. A machine-implemented method of enhancing the function of a body-implantable defibrillator, which comprises the steps of:
    determining the impedance between sensing electrodes of said defibrillator based on energy generated by the heart of the patient in whom said defibrillator is implanted;
    determining changes in said impedance between sensing electrodes of said defibrillator based on energy generated by the heart of the patient in whom said defibrillator is implanted; and
    enhancing the function of said body-implantable defibrillator based on said impedance and the changes in said impedance.

15. A device for evaluating the cardio-circulatory condition of a patient, said device comprising:
    means for determining the patient's thoracic impedance based on information solely derived from the electrical energy generated by the patient's own heart; and
    means for evaluating the cardio-circulatory condition of the patient based on patient's thoracic impedance.

16. A machine-implemented method of obtaining information about the cardiac function of a patient, said method comprising the steps of:
    continuously processing electrical signal information from an EKG during depolarization and repolarization of the patient's heart representing systole and diastole as different phases of the heart represented by said EKG, using electrical energy generated by the patient's own heart; and
    obtaining said information about the cardiac function of said patient based on said electrical signal information from said EKG as processed in said continually processing step.

17. The method of claim 16, including analyzing the impedance of the patient's heart and its changes with systole from a point close to the T-Wave of the EKG signal, and deriving information on the diastolic status of the heart derived from an impedance signal close to the R-Wave of the EKG signal.

18. The method of claim 17, including using a comparison between systole and diastole to assess the cardio-circulatory status of the patient.

19. An implantable device for monitoring the cardio-pulmonary status of a patient, comprising:
    means for determining the patient's thoracic impedance from EKG signal information acquired by the device using electrical energy generated by the patient's own heart; and
    means for monitoring the cardio-pulmonary status of the patient based on the thoracic impedance.

20. The device of claim 19, wherein said device is adapted for subcutaneous implantation.

21. The device of claim 20, including surface mounted electrodes on said device to monitor the patient's EKG.

22. The device of claim 19, including signal processing means for deriving information concerning changes in said impedance to determine the cardio-pulmonary status of the patient.

23. The device of claim 19, wherein said device is adapted for cardiac pacing, and includes means for negative feedback closed loop control of said cardiac pacing for optimization of pacing rate to match the fitness of the patient engaged in physical activity.

* * * * *